United States Patent [19]
Carpenter et al.

[11] Patent Number: 5,277,954
[45] Date of Patent: Jan. 11, 1994

[54] ADHESIVE-BACKED BREATHABLE LAYERED MATERIALS

[75] Inventors: Diane R. Carpenter, West Chester; Edward J. Daniel, Landenberg, both of Pa.; Michael J. Muehlbauer; S. Craig Newmah, both of Flagstaff, Ariz.

[73] Assignee: W. L. Gore & Associates, Inc., Newark, Del.

[21] Appl. No.: 929,050

[22] Filed: Aug. 13, 1992

[51] Int. Cl.$^5$ .................. B32B 3/00; B32B 3/12; B32B 7/12; A61F 13/15

[52] U.S. Cl. .................. 428/71; 428/159; 428/315.9; 428/316.6; 428/343; 428/354; 428/355; 428/422; 604/369; 604/378; 604/385.1

[58] Field of Search .................. 428/343, 354, 355, 71, 428/159, 315.9, 316.6, 422; 604/369, 378, 385.1

[56] References Cited

U.S. PATENT DOCUMENTS

| | | | |
|---|---|---|---|
| 3,953,566 | 4/1976 | Gore | 264/288 |
| 4,194,041 | 3/1980 | Gore et al. | 428/315 |
| 4,737,400 | 4/1988 | Edison et al. | 428/343 |
| 5,102,711 | 4/1992 | Keller et al. | 428/71 |
| 5,153,040 | 10/1992 | Faasse, Jr. | 428/354 |

OTHER PUBLICATIONS

Monsanto Data Sheet No. 1594A Gelva Multipolymer Emulsion 2582.

*Primary Examiner*—George F. Lesmes
*Assistant Examiner*—Blaine Copenheaver
*Attorney, Agent, or Firm*—Dena Meyer Weker

[57] ABSTRACT

A flexible, breathable, composite is provided. The laminate comprises a middle layer of a padding and top and bottom layer comprising a sheet of water impermeable, moisture-vapor-permeable film bonded to the middle layer and wherein at least one outer surface of the top or bottom layer is provided with a pressure-sensitive biocompatible adhesive. Preferably the top and bottom layers comprise a composite of (a) a flexible, first sheet of hydrophobic material; and (b) a continuous hydrophilic sheet attached to or penetrating the first sheet, and forming a contamination barrier. The composite is useful in diverse applications such as a padding under orthopedic casts.

13 Claims, 3 Drawing Sheets

ADHESIVE-BACKED BREATHABLE LAYERED MATERIALS

FIELD OF THE INVENTION

This invention relates to an adhesive-backed layered composite of a padding between two layers of water impermeable, moisture-vapor-permeable film, preferably porous, expanded polytetrafluoroethylene, useful, inter alia, as padding underneath orthopedic casts and braces. The layers of film surrounding the padding protect the padding, especially in applications where the padding is ordinarily susceptible to becoming wet.

BACKGROUND OF THE INVENTION

Fabrics used for underpadding for limb casts have included cotton, foams, synthetics such as polyester fiberfill and wool. The major functions of underpadding are cushioning. Most currently available underpaddings lose some of their functionality when immersed in water. Water can cause padding to compress or to shift due to weight gain. In addition, a water-saturated underpadding is not useful for transfer of moisture away from the skin. This loss of function is especially critical when the padding is worn by a person for extended periods. Prolonged wetness next to the skin causes skin breakdown and possible infection sites. It is therefore desirable to provide a padding which will not be adversely affected by exposure to water. It is also desirable to provide padding that will allow the transfer of water vapors so that perspiration and other body fluids can escape.

In the past, several methods have been used to overcome some of the drawbacks of padding. Quilting has been used to prevent padding from shifting, while maintaining high loft and bulkiness desirable in padding. Bonding padding to a fabric backing also prevents shifting. Fiberfill consists of crimped fibers to help maintain fluffiness and air space, even upon exposure to water. Hollow fibers also contain air space which add insulating value. Synthetic fibers are generally less absorbent than natural ones and have been used to wick fluids away from the skin into more absorbent backings. However, fluid saturation results in loss of function.

Large quantities of padding are used under immobilizing orthopedic casts or braces. Traditional cast underpadding consists of cotton or polyester wraps in 2 inch to 6 inch widths. Care is taken when applying the underpadding to avoid folds or creases which can cause pressure sores to the skin. The immobilizing material applied on top of this padding is usually made of plaster of Paris or polyurethane-coated fiberglass. Plaster of Paris immobilizing materials disintegrate when in contact with water and cast wearers are told not to expose the cast to any water at all. Cast wearers with fiberglass immobilizing material are usually told not to immerse the cast in water, even though polyurethane casts can withstand water immersion. If a traditionally padded polyurethane cast is immersed, the padding remains wet for many hours, and the result can be skin maceration. In some cases, this maceration can lead to skin breakdown and infection by bacteria or fungi. Cast padding material manufacturers often caution against water immersion and state that if a cast is wet, it should be completely dried with a hair dryer. This drying process can take several hours and patient compliance is extremely low. Some cast wearers use plastic bags with rubber bands around the end to keep water away from the cast while showering. Water often enters the bag and wets the padding which causes discomfort to the wearer. As a result, many cast wearers do not want to get their cast wet and spend the time they are wearing a cast without a normal shower or bath. In addition, cast wearers cannot swim or use any form of hydrotherapy.

It is widely recognized that paddings must be "breathable" to be comfortable. However, it is not necessary that air pass through the padding for it to be comfortable, only that water vapor from perspiration or other sources be transmitted from the skin outwards through the padding. "Breathability" and the ability to transport interior moisture vapor to the external environment are used interchangeably herein.

U.S. Pat. No. 5,102,711 relates to a flexible, breathable, nonlinting composite comprising a middle layer of padding and a top and bottom comprising a sheet of porous water impermeable, moisture-vapor-permeable film bonded to the middle layer. Although the properties of the composite padding are greatly desirable, the material is difficult to use in roll form as the material untangles quite easily. Moreover, during use with an orthopedic cast, the padding tends to migrate or shift under the polyurethane-fiberglass or other immobilizing material. Thus there is a need to provide an improved padding that is easier to both apply and use, as well as prevent migration or shifting under the rigid immobilizing layer and also provides improved molding and conformance to the applied area.

As used herein, the term "porous, expanded polytetrafluoroethylene" is as disclosed in U.S. Pat. No. 3,953,566. The term "breathable" as used herein means the ability to transport moisture from the humid side of a hydrophilic member and discharge the moisture on the dry side of the member, as disclosed in U.S. Pat. No. 4,194,041. U.S. Pat. Nos. 3,953,566 and 4,194,041 in addition to U.S. Pat. No. 5,102,711 are assigned to assignee herein and all are incorporated here by reference thereto. The term quilt, quilted and quilting refer to a pattern of discretely-shaped cells.

Further as used herein, the term "biocompatible" means a material that passes the following USP biological tests without causing skin irritation or sensitization: Primary Skin Irritation TA001, Intracutaneous Reactivity Test TA044-800, and Sensitization, Maximization Method (Kligman) TA006.

SUMMARY OF THE INVENTION

A flexible, breathable, composite padding having at least one pressure-sensitive adhesive surface is provided. The padding comprises a middle layer of a padding and a top and bottom layer of water-impermeable and moisture-vapor-permeable porous, expanded polytetrafluoroethylene and at least one exterior surface of the padding has a thin layer of biocompatible pressure-sensitive adhesive. The top and bottom layer of the padding each preferably comprise a flexible, first member of hydrophobic material. A continuous hydrophilic member may be joined with, i.e., attached to or penetrate the pores of the first member. The middle layer may be a synthetic material such as polyamide, polyester or polybenzimidazole fabric, woven, knitted or nonwoven. It may comprise natural fabrics such as cellulosics or wool, or may be made of down. The middle layer may alternatively be a foam, a glass cloth, glass mat or any fabric of organic or inorganic fiber. The overall padding including top and bottom layer, middle layer, and adhesive should have an moisture vapor transmission rate greater than 1000 g/m²-day.

The biocompatible pressure-sensitive adhesive applied to at least one surface of the padding must be capable of adhering repeatedly, and have a shelf life of at least 6 months. The adhesive, once applied to one side of the padding must have a sufficiently high elastic modulus to prevent its flow during storage and damage to the reverse side of the padding upon unrolling.

DETAILED DESCRIPTION OF THE INVENTION

A flexible, breathable, layered composite having at least one surface with a biocompatible pressure sensitive adhesive is provided. The composite comprises a middle layer of a padding preferably a polyamide, polyester or glass fabric, and preferably being non-flammable, and a top and bottom layer of water impermeable and moisture-vapor-permeable film. Preferably a film of porous expanded polytetrafluoroethylene is bonded in a quilted fashion as described in the Example. Preferably the top and bottom layers comprise a flexible, first member of hydrophobic material. A continuous hydrophilic member may be joined with the first member to form a barrier to passage of liquids where the hydrophobic members are both external to the middle layer.

The adhesive applied to the surface of the composite padding, is in addition to being pressure-sensitive and biocompatible, must have a shelf life of at least 6 months and be capable of adhering over repeated opening and closing of the padding. The adhesive must also be insoluble in water. The adhesive should also have a sufficiently high elastic modulus. Such that the adhesive will not flow across the padding but be capable of retaining adhesive tack without damaging the material. The adhesive is applied in a manner to maintain the breathability of the entire padding system. For non-breathable adhesives, the preferred method of application is a pattern of discontinuous spots across the padding surface. For breathable adhesives, a continuous film across the padding surface may be used.

The overall padding including the top and bottom layers, middle padding layer and adhesive preferably has a moisture vapor transmission rate of greater than 1000 g/m²-day.

The composite is useful in such diverse applications as a padded liner under orthopedic casts and braces.

A detailed description of the invention and preferred embodiments is best provided with reference to the drawings.

Figure 1:
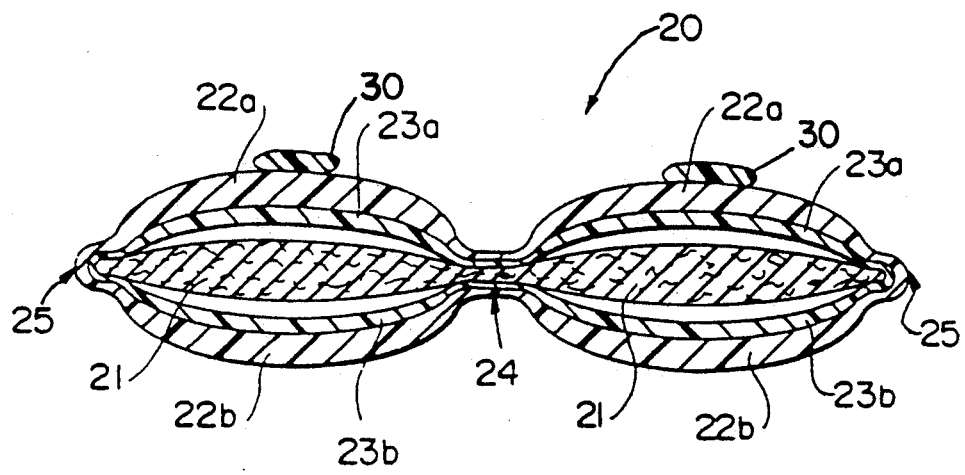
FIG. 1 is a perspective view, partly in cross-section, of a composite according to the invention.

FIG. 1 depicts a cross-section of the embodiment of the invention described in Example 1. The protective padding 20 comprises a middle layer of padding material 21 and could be in woven, non-woven or knit form, and top outer protective layer 22a and bottom outer protective layer 22b each made of a sheet of water-impermeable, water vapor-permeable material (which is porous, expanded polytetrafluoroethylene film) and each of which is coated with hydrophilic impregnant 23a and 23b (which is hydrophilic breathable polyurethane). The top and bottom outer protective layers are bonded to the middle layer 21 at quilt bond point 24 by simply thermally sealing the materials together, and at outer periphery bond seams 25. The coated water-impermeable, water vapor-permeable top and bottom outer protective layers and the middle layer are not bonded or attached to each other at any other points.

Figure 2:
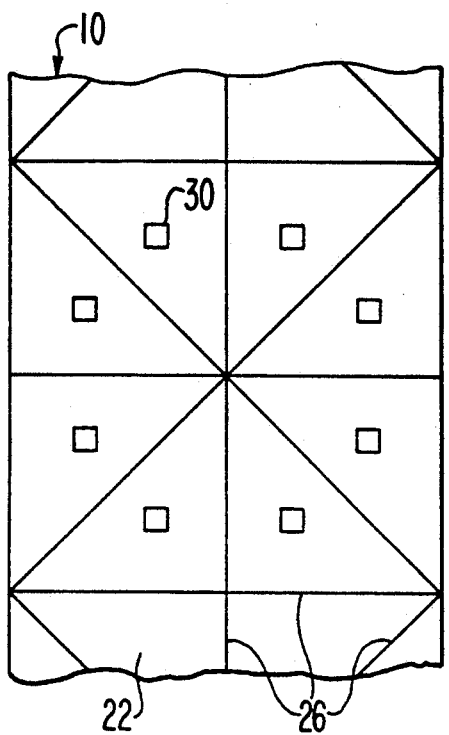
FIG. 2 is a top plan view of one embodiment of a quilted composite according to the invention.

An adhesive 30 is applied in a discontinuous manner over at least one surface of the protective padding 20. In FIGS. 1 and 2, a pattern of adhesive dots is applied to the highest point of the padding (i.e. midway between two adjacent quilt bond points 24). Alternatively, a pattern of diamond shaped or other shaped adhesive designs may be applied. Although the location of the adhesive at the midway point between two adjacent quilt bond points is preferred, the pattern of dots may also be located at the bond points 24 or other areas of the padding.

Figure 1A:
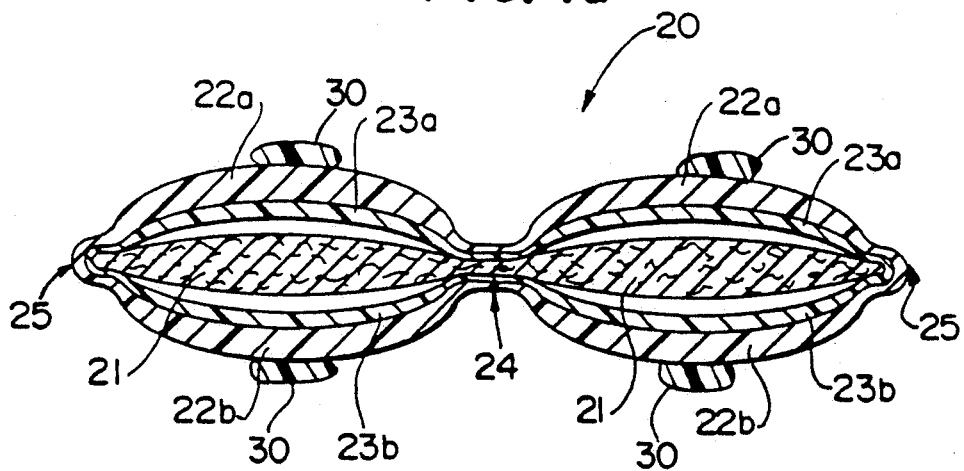
FIG. 1a is a perspective view partly in cross-section of a composite according to an alternative embodiment of the invention.

As shown in FIG. 1a, the adhesive may also be applied to both the top and bottom surfaces of the padding. Here again, the adhesive on both surfaces must possess the performance properties as described above.

Figure 4:
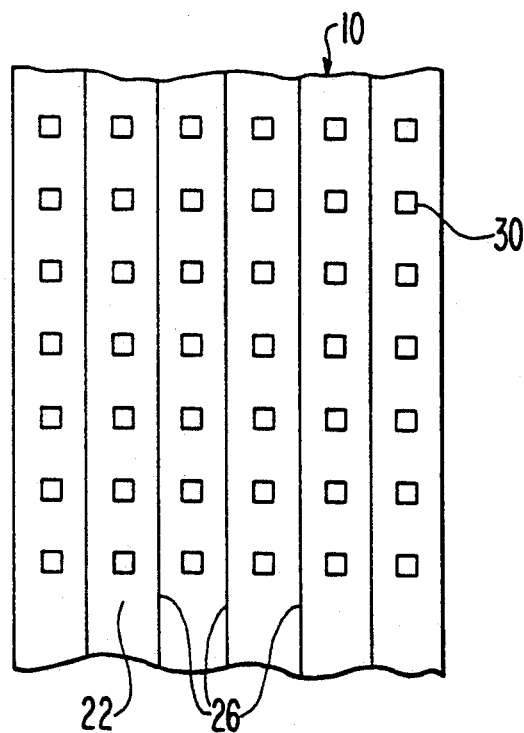
FIG. 4 is a top plan view of a third embodiment of a quilted composite.

FIG. 2 is a top plan view of a quilted embodiment 10 of padded liner for use in an orthopedic cast according to the invention, wherein the quilted pattern is in the form of triangles bounded by quilt lines 26. The adhesive dot 30 is located preferably at the peak or highest point of each triangle. FIG. 4 is an alternate embodiment having parallel quilt lines 26. Protective layer 22 is a sheet of water-impermeable water vapor-permeable material. Here, the adhesive dots 30 are located in a row adjacent the quilt lines approximately midway between the quilt lines at the softest area of the padding.

Figure 3:
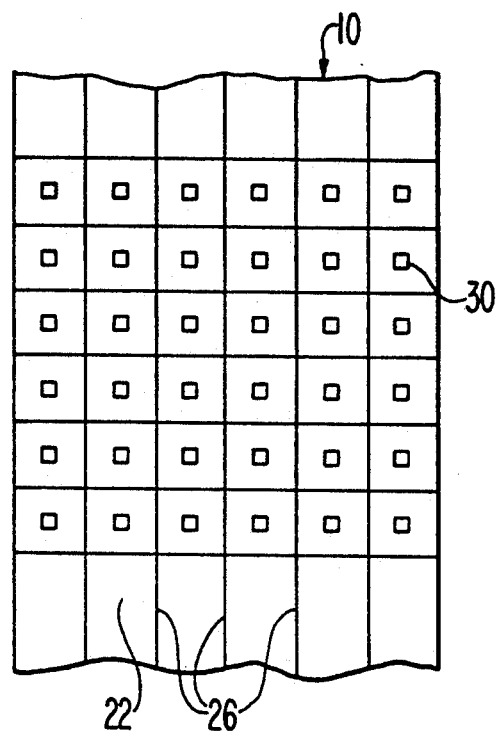
FIG. 3 is a top plan view of an alternate embodiment of a quilted composite according to the invention.

For use as a padded liner under a cast, it is desirable to divide the composite into smaller units or cells through quilting or embossing as shown in FIG. 3. This is useful not only to prevent shifting but also to protect each cell from water which may enter through a hole or defect in adjacent cells. This will allow the quilted composite to be cut or trimmed without violating the integrity of the whole pad.

For this most preferred embodiment, the adhesive dots 30 are located at the highest point of each cell, generally the mid point as shown in FIG. 3. The quilted composite can be manufactured by sealing the edges of the cells to completely encompass the padding. This sealing can be done in many ways, for example using direct heat or ultrasonic welding or adhesives.

When the composite is used as a padded liner in cast, the outer layers do not allow liquid water to pass through to the inner layers. However, water will pass through the film after it has been vaporized. Additionally, the body heat of the wearer causes this evaporation process to occur and creates a one-way path for water vapor. If the padding becomes moist, the moisture is still directed outwardly through the case, not back towards the person. Therefore, padding encapsulated in quilted composites of this invention does not experience the same water weight gain that unprotected underpadding does and the wearer does not have to wait as long to experience dryness. The skin surface dries much faster with the breathable composite laminates of this invention than with unprotected underpadding. Perspiration is allowed to pass through the breathable composites without moisture remaining on the skin. Traditional underpadding remains damp for many hours, but the padding in composites of this invention dries quickly. This provides the wearer with a great deal of comfort.

Preferably, the surface of the padding on which the adhesive is present is facing outward so that the clean padding surface is adjacent the skin of the wearer. The padding is wrapped helically around the wearer's limb or body part so that the padding slightly overlaps a previous lap of the padding and extends along the length of the wearer. In this way the adhesive on the outer surface comes in contact with the inner surface of the overlapping layer and attaches. A final rigid immobilizing structure that is made of a fiberglass or other waterproof synthetic material is then applied over the padding. Alternatively, a waterproof splint structure such as a half-cast may be applied over the padding.

By bonding the overlapping regions of the padding as described, a better conforming and molded shaped padding is provided to the wearer. In addition, by providing the bonding between laps of padding and securing the outer wrap of the rigid component, there is no shifting or migration of the padding under the rigid component of the cast as had previously been experienced by those using the padding without the adhesive surface.

A number of commercially available materials are suitable for use as the water impermeable, moisture-vapor-permeable, porous film. These materials include microporous expanded polytetrafluoroethylene as described in U.S. Pat. Nos. 3,953,566 and 4,187,390; and expanded polytetrafluoroethylene coated with hydrophilic impregnants and layers, such as described in U.S. Pat. No. 4,194,041. Alternatively, microporous polyolefin films or scrims which may be coated with or impregnated with hydrophilic polymers such as certain polyurethanes are also suitable for this use. The term "polyolefin" as used herein includes both halogen free and halogenated polyolefins, e.g., polypropylene or polytetrafluoroethylene.

A number of commercially available biocompatible pressure-sensitive adhesives are suitable for use with the padding. These adhesives include rubber based hot melt adhesives such as styrene butadiene styrene copolymers including those commercially available from H.B. Fuller Co. of St. Paul, Minn. Preferably an acrylic polymer emulsion such as Gelva® Multipolymer emulsion (GME 2582) commercially available from Monsanto Chemical Co. of St. Louis, Mo. is used. The acrylic polymer emulsion is preferred as the adhesive has a higher elastic modulus thus having less flow capability thus eliminating the need for the padding to be stored with release paper adhered to the adhesive surface. The Gelva® emulsion is said to have a shear resistance of 15 hrs. at 1 kg./0.25 sq. in. when 1 mil. of dry adhesive is applied to 1 mil. of film that is applied to stainless steel. The adhesive preferably is a formulation consisting of 30–50% acrylic emulsion and a 70–50% water-isopropyl alcohol mixture.

The adhesives are applied in a pattern of dots thereby maintaining the breathability of the overall padding. The adhesive formulation may also include surfactants such as Fluorochemical Surfactant FC171 commercially available from 3M of Minneapolis, Minn., to provide adhesive penetration into the material and thus prevent adhesive detachment.

There are many benefits of using a waterproof, breathable orthopedic cast padded liner. The products of this invention allow cast or brace wearers to shower or swim while being immobilized without special precautions or drying procedures. This is advantageous not only for hygienic purposes, but also for various therapeutic reasons. Odor and itching can be reduced for cast patients if washing is allowed on a normal schedule. Cast wearers can engage in activities which may cause profuse perspiration without the discomfort of wet underpadding. Use of hydrotherapy could aid in the healing process, as it does for some other injuries which do not require immobilization. Additional advantages are achieved by providing a waterproof, breathable orthopedic cast padded liner having an adhesive. Here migration or shifting of the padding under the rigid component of the cast is prevented. Further, the padding provides a better conforming and molded fit to the wearer.

The breathable composites of this invention can be applied to a wrap formation similar to traditional cast underpaddings such that the wraps are adhered to one another. The thinness of the film is also essential to avoid bulky folds which can cause pressure sores on the skin.

Many athletes require the use of supportive braces in which a partially rigid component is used over the padding to continue their training. Use of this padding would prevent perspiration from being trapped next to the skin following exertion. Alternatively, this padding could be incorporated directly into the brace.

MOISTURE VAPOR TRANSMISSION RATE

Moisture vapor transmission rate was determined by the teachings in U.S. Pat. No. 4,862,730 which comprises taking a weighted test cup containing a saturated salt solution sealed within a cup with a waterproof, moisture vapor permeable membrane and inserting it over the padding that is supported on a waterproof moisture vapor permeable membrane over a controlled temperature water bath.

EXAMPLE

Figure 5:
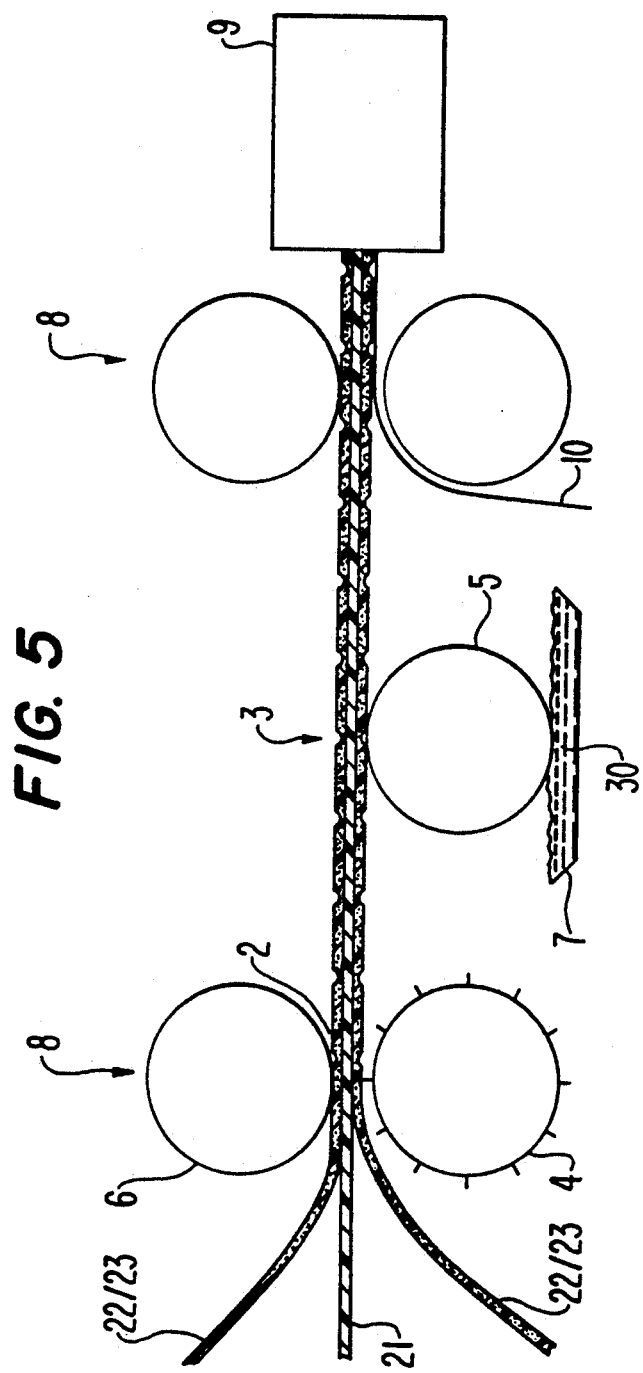
FIG. 5 is a schematic view of the processing steps.

Adhesive backed breathable layered material was provided by passing top and bottom composite sheets of porous expanded polytetrafluoroethylene (PTFE) with a hydrophilic polymer 22/23, as disclosed in U.S. Pat. No. 4,194,041 on each side of a reticulated polyurethane foam layer cover 21, commercially available from Foamex, a division of Knoll International Holding Inc. of Eddystone, Pa. The composite sheets, each having moisture vapor transmission rates of 15,000 g/m²-day, were applied to each side of the foam so as to surround the foam core with the hydrophilic side of the composite sheet facing the foam core. The layered sheets with foam core passed through a thermal embossing and quilting station as can be seen in FIG. 5 at location 2. The quilting station comprised a 0.5 inch square grid pattern steel embossing roll 4 and a Viton® covered nip roll 6. The embossing roll was heated to 270°–300° C.

The pressure sensitive adhesive formulation 30 consisted of 40% acrylic emulsion (available at Monsanto Gelva #2582), added to a mixture of 30% isopropyl alcohol and 30% water. The adhesive material was applied to the layered material by a kiss roll coating method as shown at location 3. This method comprises a rotating steel roller 5 that contacts a trough 7 filled with adhesive. The layered material contacts the roller 5 in a tangential manner such that the adhesive is applied only at the highest or peak part of each quilt pillow. The pressure sensitive adhesive treated material then passed through a nip station 9 at location 8 where a silicone coated paper release paper 10 was applied.

The adhesive treated layered material/liner combination was then passed through a radiant infrared oven (temperature of approximately 120° C.) at location 9 to drive off the water and alcohol.

The moisture vapor transmission rate of the padding made in accordance with this particular example was 1418 g/m$^2$-day.

While the invention has been disclosed herein in connection with certain embodiments and detailed descriptions, it will be clear to one skilled in the art that modifications or variations of such details can be made without deviating from the gist of this invention, and such modifications or variations are considered to be with the scope of the claims hereinbelow.

We claim:
1. A flexible, breathable, composite comprising:
   a) a middle layer of padding;
   b) a top and bottom layer each comprising water impermeable and moisture-vapor-permeable film as the external surfaces, said top and bottom layers encapsulating said middle layer by sealing the open edges of the top and bottom layers; and
   c) at least one of the top or bottom layers at their exterior surface is further provided with a layer of pressure-sensitive, biocompatible adhesive in a manner sufficient to maintain the breathability of said composite, wherein the at least one of the top or bottom layers is a porous expanded polytetrafluoroethylene film.

2. The composite of claim 1 wherein said top and bottom layers each have a continuous hydrophilic layer joined to the film, said hydrophilic layer forming a contamination barrier.

3. The composite of claim 2 wherein the hydrophilic layer is a polyurethane.

4. The composite of claim 1 wherein said middle layer is foam.

5. The composite of claim 1 wherein said middle layer is polyester.

6. The composite of claim 1 wherein said middle layer is wool.

7. The composite of claim 1 which the top and bottom layers of porous film define discrete quilt patterns in which the middle layer and top and bottom layers are compressed and bonded along the peripheral boundaries of the quilt pattern.

8. An orthopedic immobilizer containing the composite of claim 1.

9. The composite of claim 1 wherein the biocompatable adhesive is applied in a pattern of designs selected from the group consisting of dots, diamonds, squares and triangles.

10. The composite of claim 1 wherein both outside surfaces of the top and bottom layers are provided with a layer of pressure-sensitive, biocompatible adhesive.

11. The composite of claim 1 wherein the adhesive is an acrylic polymer emulsion.

12. The composite of claim 10 wherein the adhesive is an acrylic polymer emulsion.

13. The composite of claim 1 wherein the adhesive is a formulation consisting of 40% acrylic emulsion, 30% isopropyl alcohol and 30% water.

* * * * *

UNITED STATES PATENT AND TRADEMARK OFFICE
CERTIFICATE OF CORRECTION

PATENT NO. : 5,277,954

DATED : January 11, 1994

INVENTOR(S) : Diane R. Carpenter, Edward J. Daniel, Michael J. Muehlbauer, S. Craig Newman It is certified that error appears in the above-identified patent and that said Letters Patent is hereby corrected as shown below:

On the Title Page:
Item [75]

Kindly change "Craig Newmah" to --Craig Newman--

Column 4, line 13:
   Change "an" to --a--

Column 5, line 19:
   Change "modulus.  Such" to --modulus such--

Column 7, line 29:
   Change "adjacent the skin" to --adjacent to the skin--.

Signed and Sealed this

Thirty-first Day of May, 1994

*Attest:*

BRUCE LEHMAN

*Attesting Officer*    *Commissioner of Patents and Trademarks*